United States Patent [19]

Yu et al.

[11] 4,363,815

[45] * Dec. 14, 1982

[54] ALPHA HYDROXYACIDS, ALPHA KETOACIDS AND THEIR USE IN TREATING SKIN CONDITIONS

[76] Inventors: Ruey J. Yu, 4 Lindenwold Ave., Ambler, Pa. 19002; Eugene J. Van Scott, 1138 Sewell La., Rydal, Pa. 19046

[ * ] Notice: The portion of the term of this patent subsequent to Apr. 22, 1992, has been disclaimed.

[21] Appl. No.: 145,240

[22] Filed: Apr. 30, 1980

Related U.S. Application Data

[60] Continuation-in-part of Ser. No. 60,460, Jul. 25, 1979, abandoned, which is a continuation-in-part of Ser. No. 870,114, Jan. 17, 1978, Pat. No. 4,197,316, which is a division of Ser. No. 720,835, Sep. 7, 1976, Pat. No. 4,105,783, which is a continuation-in-part of Ser. No. 598,224, Jul. 23, 1975, Pat. No. 4,021,572.

[51] Int. Cl.$^3$ .................... A61K 31/19; A61K 31/40
[52] U.S. Cl. ................... 424/274; 424/279; 424/283; 424/317; 424/319; 424/338; 424/DIG. 4
[58] Field of Search ............... 424/318, 317, 274, 319

[56] References Cited

U.S. PATENT DOCUMENTS

| | | | |
|---|---|---|---|
| 2,118,566 | 5/1938 | Miles | 424/317 X |
| 3,124,506 | 3/1964 | Holman | 424/317 X |
| 3,879,537 | 4/1975 | Van Scott et al. | 424/283 |
| 3,988,470 | 10/1976 | Van Scott et al. | 424/283 |

*Primary Examiner*—Leonard Schenkman
*Attorney, Agent, or Firm*—Le Blanc, Nolan, Shur & Nies

[57] ABSTRACT

Preventive as well as therapeutic treatment to alleviate the symptoms of skin disorders associated with disturbed keratinization or inflammation with one or more alpha or beta hydroxy-acids and alpha or beta ketoacids is disclosed. The alpha or beta hydroxyacids and alpha or beta ketoacids of this invention include free acids, or peroxide, amide, lactone, anhydride, ester, polymer, organic or inorganic salt forms thereof. Therapeutic compositions of this invention may include one or more of the alpha or beta hydroxyacids or the alpha or beta ketoacids of this invention present in a total amount of from 0.1 to 40 percent in an acceptable vehicle. The compositions are particularly useful for the topical treatment of skin conditions such as dry skin, ichthyosis, palmar and plantar hyperkeratosis, dandruff, Darier's disease, lichen simplex chronicus, keratoses, acne, psoriasis, eczema, pruritus and possibly warts and herpes.

12 Claims, No Drawings

ALPHA HYDROXYACIDS, ALPHA KETOACIDS AND THEIR USE IN TREATING SKIN CONDITIONS

This application is a continuation-in-part of our U.S. patent application Ser. No. 60,460, filed July 25, 1979 now abandoned, which was in turn a continuation-in-part of our U.S. patent application Ser. No. 870,114 filed Jan. 17, 1978, now U.S. Pat. No. 4,197,316, which was a division of our U.S. patent application Ser. No. 720,835, filed Sept. 7, 1976, now U.S. Pat. No. 4,105,783 which application in turn was a continuation-in-part of our U.S. patent application Ser. No. 598,224, filed July 23, 1975, now U.S. Pat. No. 4,021,572. This patent application is also related to our U.S. Pat. Nos. 4,105,782; 3,988,470, 3,984,566; 3,920,835 and 3,879,537. This application is also related to our U.S. patent application Ser. No. 948,489 filed Oct. 4, 1978 now U.S. Pat. No. 4,234,599. The disclosures of the above patents and patent applications are hereby incorporated by reference.

This invention relates generally to the treatment of skin disorders, and specifically, to a broad range of compounds found to be effective against disease conditions characterized by disturbed keratinization. As will be subsequently described in detail, we initially discovered that certain related organic acids and their reaction products with certain organic bases were effective in the topical treatment of disease conditions such as ichthyosis, eczema, dry skin, and palmar and plantar keratoses. We have now discovered that broad families of related compounds including those initially discovered are widely effective in therapeutic treatment of disease conditions characterized as disturbed keratinization and skin inflammation.

In our application Ser. No. 870,114, filed Jan. 17, 1978, the disclosure of which is hereby incorporated by reference, there is described the discovery that a reaction product of certain alpha hydroxyacids and related compounds and certain organic amines or ammonium hydroxide is effective in the topical treatment of dry skin conditions.

Specifically, the acids and related compounds described therein are citric acid; glycolic acid; glucuronic acid; galacturonic acid; lactones, such as glucuronolactone, and gluconolactone; alpha hydroxybutyric acid; alpha hydroxyisobutyric acid; lactic acid; malic acid; mandelic acid; mucic acid; pyruvic acid; esters thereof, such as methyl pyruvate and ethyl pyruvate; compounds related thereto, such as beta phenyllactic acid and beta phenylpyruvic acid; beta hydroxybutyric acid; saccharic acid, tartaric acid; and tartronic acid.

Basic reactants described therein include ammonium hydroxide, organic primary, secondary or tertiary amines, such as alkylamines, alkanolamines, diamines, dialkyl amines, dialkanolamines, dialkylalkanolamines, and alkyl dialkanolamines wherein the alkyl or alkanol substituent has from 1-to-8 carbon atoms.

Representative amines, as also described, were methylamine, ethylamine, monoethanolamine, monoisopropanol amine, ethylene-diamine, 1,2-diaminopropane, dimethylamine, diethylamine, diethanolamine, diisopropanolamine, N-methylethanolamine, N-ethylethanolamine, triethylamine, triethanolamine, N-methyldiethanolamine, and triisopropylamine.

In our copending patent application Ser. No. 948,489 filed Oct. 4, 1978, the disclosure of which is hereby incorporated by reference, we describe our discovery that certain free acids, related compounds and reaction products with certain organic or inorganic bases were effective upon topical application to alleviate the symptoms of actinic and nonactinic keratoses.

Specifically, the free acids and related compounds described were citric acids; glycolic acid; glucuronic acid; gluconic acid; galacturonic acid; glucoheptonic acid; lactones, such as glucoheptono 1,4-lactone, gluconolactone, glucuronolactone; alpha hydroxybutyric acid; alpha hydroxyisobutyric acid; alpha hydroxyisocaproic acid; alpha hydroxyisovaleric acid; lactic acid; atrolactic acid; malic acid; mandelic acid; mucic acid; pyruvic acid; esters thereof, such as methyl pyruvate, ethyl pyruvate, and isopropyl pyruvate; saccharic acid; its lactone, saccharic acid 1,4-lactone; tartaric acid, tartronic acid; and related compounds, such as beta hydroxybutyric acid; beta phenyllactic acid, beta phenylpyruvic acid.

This list of acids and related materials disclosed in our application Ser. No. 948,489, includes the compounds identified in application Ser. No. 870,114, and in addition, gluconic acid, glucoheptonic acid, glucoheptono 1,4-lactone, alpha hydroxyisocaproic acid, alpha hydroxyisovaleric acid, atrolactic acid, isopropyl pyruvate, and saccharic 1,4-lactone. This list then totals twenty-nine related compounds found to be effective against skin keratoses.

The basic compounds enumerated as reactants also include the compounds listed in prior application Ser. No. 870,114, and additionally also included as a class quaternary amine compounds having from 1-to-8 carbon atoms. Specifically, the class includes basic choline.

Subsequently, in our U.S. patent application Ser. No. 60,460, filed July 25, 1979, the disclosure of which is hereby incorporated by reference, we described our discovery that in addition to the compounds and compositions described in our U.S. patent application Ser. No. 948,489 these compounds and other related compounds were effective against dry skin. The additional compounds include isocitric acid, dihydroxymaleic acid, dihydroxytartaric acid, dihydroxyfumaric acid, galactonic acid, pantoic acid, glyceric acid, benzoylformic acid, methyl benzoylformate, ethyl benzoylformate, $\beta$-hydroxypyruvic acid, $\beta$-hydroxypyruvic acid phosphate, galatonolactone, mucic acid lactone, and pantoyllactone.

The compounds were found to be effective as free acids, lactones, esters, anhydrides, or as amides or salts formed as reaction products with ammonium hydroxide or with the organic bases previously described. It was also found that an effective reaction product could be produced with inorganic bases such as sodium or potassium hydroxide.

In our patent application Ser. No. 869,351, filed Jan. 13, 1978 and entitled "Alpha hydroxyretinoic, alpha ketoretinoic acid and mixtures and their use in treating skin conditions", we described and claimed the usefulness of certain alpha hydroxyacids and alpha ketoacids of up to twenty carbon atoms for the treatment of conditions such as dry skin, ichthyosis, palmar and plantar hyperkeratosis, psoriasis, eczema, Darier's disease and lichen simplex chronicus.

It has now been discovered that the inventions described in our above identified Patents and patent applications have much broader therapeutic applicability. The therapeutic applicability includes topical treatment against a variety of skin inflammation and skin keratinization disturbances and specifically in treating skin conditions and disorders such as dry skin, ichthyosis, palmar and plantar hyperkeratosis, dandruff, Darier's disease, lichen simplex chronicus, keratoses, acne, psoriasis, eczema, pruritus and warts and herpes.

It has also been discovered that many additional related compounds as free acids, esters, lactones, amides, salts, anhydrides and polymer forms are of therapeutic value against a variety of skin inflammation and skin keratinization disturbances. The additional compounds include, as will be subsequently explained, all hydroxy and keto analogues of amino acids whether naturally occuring in proteins, or not. For example, one such compound is methionine hydroxy analogue (Merck Index 4743), a sulfur containing alpha hydroxyacid chemically known as 2-hydroxy-4(methylthio) butanoic acid. This compound is known and used in the form of its calcium salt as an additive in poultry feed.

In fact, many of the alpha hydroxyacids and alpha ketoacids described in our above identified Patents and patent applications are hydroxy and keto analogues of amino acids. For example, glycolic acid is an hydroxy analogue of glycine. Lactic acid and pyruvic acid are, respectively, hydroxy and keto analogues of alanine. Glyceric acid is an hydroxy analogue of serine. Malic acid is a hydroxy analogue of aspartic acid. Beta phenyllactic acid and beta phenylpyruvic acid are, respectively, hydroxy and keto analogues of phenylalanine. Alpha hydroxyisovaleric acid is an hydroxy analogue of valine, and alpha hydroxyisocaproic acid is an hydroxy analogue of leucine.

It has also been found that cyclic alpha hydroxyacids and alpha ketoacids not previously disclosed are of therapeutic value also against a variety of skin disorders. For example, quinic acid has been found to be markedly effective in the topical treatment of dry skin.

The alpha hydroxyacids and alpha ketoacids of the instant invention may be utilized either as a major active ingredient or as an additive to enhance the therapeutic effect of other active drugs. One example is the use of alpha hydroxyacids or alpha ketoacids as an additive to enhance the anti-inflammatory action of corticosteroids. Another example is the incorporation of certain alpha hydroxyacids as stabilizers for dithranol in topical formulations.

In our U.S. patent application Ser. No. 65,332, filed Aug. 9, 1979, and entitled "Additives Enhancing Topical Corticosteroid Action", we described and claimed our discovery that the compounds described in our U.S. patent application Ser. No. 60,460 also unexpectedly improve the therapeutic activity of certain antiinflammatory agent. In our U.S. patent application Ser. No. 78,181, filed Sept. 24, 1979, and entitled "Dithranol Compositions Stabilized with Alpha Hydroxyacids", we describe our discovery that compositions containing the antiinflammatory agent dithranol may be stabilized for prolonged storage with the additives described in our U.S. patent application Ser. No. 65,332. Accordingly, the disclosures of our above patent applications are also hereby incorporated by reference.

In accordance with the present invention, the alpha or beta hydroxyacids and ketoacids which are incorporated in cosmetic or therapeutic compositions for topical application to alleviate the symptoms of skin conditions or skin disorders are grouped in the following three classes:

The first class of compounds is $\alpha$ or $\beta$ hydroxyacids containing only one carboxylic group as shown by the following chemical structures:

$$R(CR_1R_2)_m (CR_3OH)_n COOH$$

m=0, 1, 2, 3, 4, 5, 6, or 7
n=1, 2, 3, 4, 5, 6, or 7
R, $R_1$, $R_2$, $R_3$, =H, CHO, alkyl or aryl of 1 to 7 carbon atoms The $\alpha$ or $\beta$ hydroxyacids of this class may be chemically in the form of a straight chain, a ring or a polymer. When in a ring, R and one of $R_1$ or $R_3$ may be omitted from the structure. For example, quinic acid has a structure of $(CHOH)_3 (CH_2)_2$ COH COOH. A well known polymer of an $\alpha$ or $\beta$ hydroxyacid is linear lactic acid polymer which contains approximately 3 lactic acid groups.

Many polyhydroxycarboxylic acids, especially the carbohydrates can exist either as free acids or a lactones or as both forms, and can be isolated as crystalline products. For example, D-gluconic acid (Merck Index 4287) can be isolated as a free acid mp. 131° C. or as a 1,5-lactone mp. 153° C., known as D-gluconolactone (Merck Index 4288). Commercially, however, it is only available as D-gluconolactone. A freshly prepared 1% aqueous solution of D-gluconolactone has pH 3.6 which changes to pH 2.5 within 2 hours. This is because D-gluconolactone reacts with water to form gluconic acid in aqueous solution. Therefore, the free acid and lactone forms of a polyhydroxycarboxylic acid are in essence inseparable.

The $\alpha$ or $\beta$ hydroxyacids may be present as free acids, peroxides, lactones, amides, esters or salts formed by reacting the compound with ammonium hydroxide, organic or inorganic base.

The representative $\alpha$ or $\beta$ hydroxyacids of this class which have not been described in our previous Patents and patent applications are listed below:
1. 2-hydroxy-3-methylpentanoic acid, a hydroxy analogue of isoleucine
2. 2,3-dihydroxybutanoic acid, a hydroxy analogue of threonine.
3. 2-hydroxy-3-mercaptopropanoic acid, a hydroxy analogue of cysteine.
4. 3,3-dithiobis (2-hydroxypropanoic acid), a hydroxy analogue of cystine.
5. 2-hydroxy-4-(methylthio) butanoic acid, a hydroxy analogue of methionine.
6. 2-hydroxy-4-(methylsulfoxide) butanoic acid, another hydroxy analogue of methionine.
7. 2-hydroxy-4-(methylsulfonyl) butanoic acid, still another hydroxy analogue of methionine.
8. 2-hydroxy-5-guani dopentanoic acid, a hydroxy analogue of arginine.
9. 2,6-dihydroxyhexanoic acid, a hydroxy analogue of lysine.
10. 2-hydroxy-6-aminohexanoic acid, another hydroxy analogue of lysine.
11. 2,5,6-trihydroxyhexanoic acid, a hydroxy analogue of hydroxy lysine.
12. 2,5-dihydroxy-6-aminohexanoic acid, another hydroxy analogue of hydroxy lysine.
13. 2-hydroxy-3-(4-imidazolyl) propanoic acid, a hydroxy analogue of histidine.
14. 2-hydroxy-3-(4-hydroxyphenyl) propanoic acid, a hydroxy analogue of tyrosine.

15. 2-hydroxy-3-(3' indolyl) propanoic acid, a hydroxy analogue of tryptophan.
16. 2-hydroxy-4-mercaptobutanoic acid, a hydroxy analogue of homocysteine.
17. 4,4'-dithiobis (2-hydroxybutanoic acid), a hydroxy analogue of homocystine.
18. 2,4-dihydroxybutanoic acid, a hydroxy analogue of homoserine.
19. 2-hydroxy-3-sulfinopropanoic acid, a hydroxy analogue of cysteine sulfinic acid.
20. 3-aminolactic acid, a hydroxy analogue of 3-aminoalanine.
21. 2,4-dihydroxybutanoic acid, a hydroxy analogue of 2,4-diaminobutanoic acid.
22. 2-hydroxy-2-methyl-butanoic acid, a hydroxy analogue of isovaline.
23. 2,5-dihydroxypentanoic acid, a hydroxy analogue of ornithine.
24. 2-hydroxy-5-ureidopentanoic acid, a hydroxy analogue of citrulline.
25. 2-hydroxy-6-ureidohexanoic acid, a hydroxy analogue of homocitrulline.
26. 2-hydroxy-3-(5'-hydroxyindolyl) propanoic acid, a hydroxy analogue of 5-hydroxytryptophan.
27. 3-(3',4'-dihydroxyphenyl) lactic acid, a hydroxy analogue of dopa.
28. 3-(3'-iodo-4'-hydroxypenyl) lactic acid, a hydroxy analogue of 3-iodotyrosine.
29. 3-(3',5'-diiodo-4'-hydroxyphenyl) lactic acid, a hydroxy analogue of 3,5-diiodotyrosine.
30. Hydroxy analogue of thyroxine:

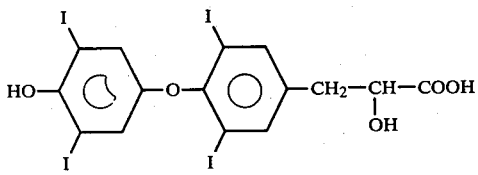

31. Hydroxy analogue of thyronine:

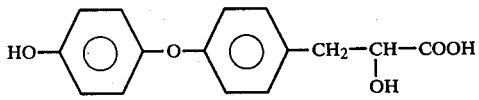

32. Quinic acid.
33. 3-hydroxypropanoic acid.
34. Aldonic acids: including trihydroxy butanoic acid, tetrahydroxy-pentanoic acid, pentahydroxyhexanoic acid and hexahydroxyheptanoic acid.
35. Uronic acids: including glyceruric acid, threuric acid, erythreuric acid, xyluric acid, lyxuric acid, arabinuric acid, riburic acid, iduric acid, guluric acid, mannuric acid, altruric acid, alluric acid and taluric acid.
36. 2-hydroxy-3-sulfonopropanoic acid, a hydroxy analogue of cysteic acid.
37. 2-hydroxy-3-thio-s-(3'-hydroxy-1',1'-dimethylpropyl) propanoic acid, a hydroxy analogue of felinine.
38. P-hydroxyphenylglycolic acid.
39. O-acetylmandelic acid.
40. O-acetylmandelic acid peroxide.

Since sulfonic is an isosteric group relative to carboxylic acid i.e., they have similar steric arrangements and electronic configurations, certain hydroxysulfonic acids may also be included in the above listing. Examples are 2-hydroxymethylsulfonic acid, an hydroxy analogue of taurine and hydroxymethylsulfonic acid, a sulfonic analogue of glycolic acid.

The second class of compounds is α or β hydroxy polycarboxylic acids with the following chemical structure:

$$(CRX)_m (COOH)_n$$

X = OH or H when m ≧ 2 and with one OH present.
m = 1, 2, 3, 4, 5, 6
n = 2, 3, 4
R = H, CHO, alkyl or aryl of 1 to 7 carbon atoms The α or β hydroxy polycarboxylic acids may be present as free acids, peroxides, lactones, amides, esters or salt forms of either an open chain structure or as a ring form. For example, whereas malic acid is a monohydroxy dicarboxylic acid of an open chain structure, saccharic acid is a tetrahydroxydicarboxylic acid of a ring form commercially available as saccharic acid 1,4-lactone. The open chain structure of saccharic acid is also commercially available but as a salt form.

Many hydroxypolycarboxylic acids, especially the carbohydrates could exist as free acids or lactones or both, and can be isolated as crystalline products. For example, D-saccharic acid also known as D-glucaric acid (Merck Index 4279) can be isolated as a free acid mp. 125°–126° C. or as a 1,4-lactone monohydrate mp. 90° C. As mentioned above, D-saccharic acid is not commercially available as a free acid. It is expressed that when D-saccharic acid 1,4-lactone is dissolved in water some lactone will react with water to form free acid. This will be evidenced by the decreasing pH of a freshly prepared solution. An equilibrium will be eventually reached wherein the aqueous solution will contain certain proportions of acid and 1,4-lactone of D-saccharic acid. Therefore, the free acid and lactone forms of a hydroxypolycarboxylic acid are actually inseparable.

The representative α or β hydroxy polycarboxylic acids which have not been described in our previous Patents and patent applications are listed below:

1. 2-hydroxysuccinamic acid, a hydroxy analogue of asparagine.
2. 2-hydroxyglutaric acid, a hydroxy analogue of glutamic acid.
3. 2-hydroxyglutaramic acid, a hydroxy analogue of glutamine.
4. 2-hydroxy-4-aminoglutaric acid, a hydroxy derivative of glutamic acid.
5. 2,4-dihydroxyglutaric acid, a hydroxy analogue of hydroxyglutamic acid.
2,3-dihydroxy-4-aminoglutaric acid, a dihydroxy derivative of glutamic acid.
7. 2-hydroxy-3-thio-s-(1'-carboxy-2'-methylpropyl) propanoic acid, a hydroxy analogue of isovalthine.
8. 2-hydroxyadipic acid, a hydroxy analogue of 2-aminoadipic acid.
9. 2,6-dihydroxypimelic acid, hydroxy analogue of 2,6-diaminopimelic acid.
10. 4-hydroxy-4-methylglutamic acid.
11. 3,4-dihydroxyglutamic acid.
12. 4-hydroxyglutamic acid.
13. Aldaric acids: including ribaric acid, arabaric acid, xylaric acid, lyxaric acid, allaric acid, altraric acid, mannaric acid, gularic acid, idaric acid and talaric acid.

The third class of compounds is α or β ketoacids as shown by the following chemical structure:

R₁-CO(CHR₂)ₙ COOH n = 0,1

R₁ = H, CHO, alkyl or aryl of 1 to 7 carbons atoms with or without other elements such as N,O,S,P,-F,I, Br and Cl.

R₂ = H, OH, CHO, alkyl or aryl of 1 to 7 carbon atoms with or without other elements such as N,O,S,P,F,I, Br and Cl.

The α or β ketoacids may be present as free acids, lactones, amides, anhydrides, esters or salt forms of either an open chain structure or as a ring form.

The representative α or β ketoacids which have not been described in our previous Patents and patent applications are listed below:
1. Acetopyruvic acid.
2. Acetyl pyruvic acid.
3. β-fluoropyruvic acid.

It has previously been established through tests on humans having dandruff, pruritus, palmar and plantar hyperkeratosis, dry skin, ichthyoses, Darier's disease, acne or psoriasis that topical application of alpha hydroxyacids in a concentration of from 1-to-10 percent is therapeutically effective, when applied on a regular basis, to cause, within about two-to-four weeks, a substantial improvement with return of the affected areas to a normal state. These tests were described in our above identified Patents and patent applications.

The alpha or beta hydroxyacids and ketoacids of this invention are also useful in treatment of various skin disorders. These disorders would include disturbed keratinizations and inflammatory diseases such as dry skin, ichthyoses, palmar and plantar hyperkeratosis, dandruff, acne, Darier's disease, pruritus, lichen simplex chronicus, keratoses, warts, herpes, psoriasis and eczema.

Generally, the alpha or beta hydroxyacids and ketoacids which are useful in treatment of various skin conditions according to this invention may be formulated in solution, lotion, gel, shampoo, spray, stick, powder, cream or ointment form containing from 0.1 to 40 percent by weight of the active ingredients in a pharmaceutically or cosmetically acceptable vehicle.

Accordingly, it is an object of this invention to provide cosmetic as well as medicinal compositions containing at least one alpha or beta hydroxyacid or ketoacid, which when topically applied will substantially alleviate the symptoms of various skin disorders.

It is another object of this invention to provide a method for treating various skin conditions with a non-toxic solution, lotion, gel, shampoo, spray, stick, powder, cream or ointment of the present invention.

It is still another object to provide a safe and efficient method for treating the symptoms of various skin conditions through regular topical application of a cosmetic as well as medicinal composition which will promote healing within about two-to-four weeks.

It is yet another object of this invention to provide a method for formulating a cosmetic as well as medicinal composition in solution, lotion, gel, shampoo, spray, stick, powder, cream or ointment which when topically applied at least regularly to skin areas prone to lesions of skin disorders will prevent the development of such disorders or restore a normal healthy skin condition.

PREPARATION OF THE THERAPEUTIC COMPOSITIONS

To prepare the composition of the present invention the alpha or beta hydroxyacid or ketoacid is initially dissolved in water or ethanol. The concentration of the alpha or beta hydroxyacid or ketoacid may range from 0.1 to 40 percent by weight of the total composition. The preferred concentration range, however, is from 0.2 to 20 percent. The solution thus prepared may then be admixed in a conventional manner with commonly available cream or ointment bases such as hydrophilic ointment.

A partially neutralized alpha or beta hydroxyacid or ketoacid composition may be prepared as follows. The aqueous or alcoholic solution of an alpha or beta hydroxyacid or ketoacid as prepared above is cooled externally with an ice-water bath. Ammonium hydroxide organic or inorganic base is added to the solution until the pH ranges from 2.0 to 6.0, as desired. This slightly acidic solution is then typically admixed with oil-in-water or water-in-oil emulsion vehicle.

To prepare a solution, the alpha or beta hydroxyacid or ketoacid is directly dissolved in a mixture of water, ethanol and propylene glycol in a volume ratio preferably of 30:50:20 respectively.

A typical gel preparation of this invention utilizes at least one of the alpha or beta hydroxyacid or ketoacid, dissolved in a mixture of water, ethanol and propylene glycol in a volume ratio of 40:40:20 respectively. A gelling agent such as hydroxyethylcellulose, hydroxypropylcellulose or hydroxypropylmethylcellulose is then added to the mixture with agitation. The preferred concentration of the gelling agent may range from 0.1 to 3 percent by weight of the total composition.

Certain alpha or beta hydroxyacids or ketoacids are commercially available as acid, amide, lactone, ester or salt forms. For example, quinic acid is available as a free acid form. However, a methionine hydroxy analogue, 2-hydroxy-4-(methylthio) butanoic acid, is available only as its calcium salt. To prepare a therapeutic composition of the present invention, the methionine hydroxy analogue calcium salt is preferably dissolved in a dilute hydrochloric acid solution. The pH of the solution may range from 2.0 to 6.0. The acidic solution thus prepared is then admixed with a cream or an ointment.

The prophylactic as well as therapeutic composition may be prepared in a form of solution, lotion, gel, shampoo, spray, stick, powder, cream or ointment. In these instances, cosmetically acceptable ingredients are incorporated into the lotion, powder, stick, shampoo or spray formulation as will be obvious to those skilled in the art.

The following are illustrative examples of formulations or compositions according to this invention. Although the examples utilize only selected formulations useful according to this invention, it should be understood that the following examples are illustrative and not limited. Therefore, any of the aforementioned acids, amides, lactones, anhydrides, esters or salts may be substituted according to the teachings of this invention in the following examples.

EXAMPLE 1

The following is a typical example for formulating a composition containing water soluble hydroxyacids or ketoacids.

Quinic acid 5 gm is dissolved in 15 ml of water, and the solution is admixed with 80 gm of hydrophilic ointment, U.S.P. Agitation is continued until a uniform consistency is obtained.

EXAMPLE 2

2-hydroxy-4-(methylthio) butanoic acid 5% cream is formulated as follows.

Commercially available methionine hydroxy analogue calcium salt 5 gm is dissolved in 5 ml 4 N HCl, and the solution is admixed with 90 gm of hydrophilic ointment, U.S.P. Agitation is continued until a uniform consistency is obtained.

EXAMPLE 3

2-hydroxy-4-(methylthio) butanoic acid 10% gel is formulated as follows.

Methionine hydroxy analogue calcium salt 10 gm is dissolved in 10 ml 4 N HCl, and the solution is admixed with 18 ml of water, 40 ml of ethanol and 20 ml of propylene glycol. Hydroxypropylcellulose 2 gm is added to the mixture with agitation. Continue agitation until a uniform gel is formed.

EXAMPLE 4

The following is a typical example for formulating an oil-in-water emulsion containing an ammonium salt form of hydroxyacids.

PART A

Polyoxyethylene (40) stearate: 3 gm
Polyoxyethylene (20) sorbitan monooleate: 2 gm
Glycerylmonostearate: 5 gm
Cetyl alcohol: 3 gm
Beeswax: 3 gm
Mineral oil: 2 gm

PART B

Water: 63 ml
Propylene glycol: 5 ml
Glycerol: 3 ml
Sorbitol: 3 gm
Quinic acid: 5 gm
Ammonium hydroxide: 1.8 ml
Carbomer 934: 0.2 gm Heat both Part A and Part B to 75° C. Add Part B slowly to Part A with agitation. Continue agitation until a uniform consistency is obtained. The pH of the cream is 4.9.

EXAMPLE 5

The following is a typical example for formulating a water-in-oil emulsion containing hydroxyacids.

PART A

Sorbitan sesquioleate: 10 gm
Petrolatum: 15 gm
Mineral Oil: 15 gm
Isopropyl myristate: 10 gm
Beeswax: 15 gm

PART B

Water: 23 ml
Propylene glycol: 5 ml
Sorbitol: 3 gm
Glycerol: 3 ml
Magnesium hydroxide: 0.1 gm Heat both Part A and Part B to 80° C. Add Part B slowly to Part A with agitation. After the mixture is congealed add 10% phoshoric acid 0.5 ml and aluminum chlorohydroxide 0.5 gm. Quinic acid 1 gm is then added to the cream. Continue agitation until a uniform consistency is obtained. This composition with a pH of 4.0 contains 1% active ingredient.

EXAMPLE 6

2-hydroxy-4-(methylsulfonyl) butanoic acid, a hydroxy analogue of methionine in sulfone form may be synthesized as follows.

Commercially available DL-methionine hydroxy analogue calcium salt 50 gm is slowly added to 100 ml of concentrated nitric acid. The temperature of the mixture is kept at 55°-to-60° C. during the entire period of oxidation. After the evolution of $NO_2$ has subsided the mixture is cooled externally with an ice-water bath, and is adjusted to pH 1.5 with 10 N NaOH. The mixture is filtered to remove the solid material thus formed and the filtrate is lyophilized to remove the water. The yellowish semisolid thus obtained is extracted with 400 ml of methanol, and the filtered methanolic solution is evaporated at 40° C. in vacuum. The residue thus obtained is extracted with hot ethanol and the filtered ethanolic solution is evaporated at 45° C. in vacuum to afford 50 gm of light yellowish syrup. 2-hydroxy-4-(methylsulfonyl) butanoic acid thus synthesized is practically pure as shown by infrared spectroscopy and by thin-layer chromatography with a mobility of 0.60 on a solvent system of benzene: methanol, 1:1.

EXAMPLE 7

A typical composition in a solution form containing a hydroxyacid is formulated as follows.

2-hydroxy-4-(methylsulfonyl) butanoic acid 5 gm synthesized according to Example 6 is dissolved in 35 ml of water. The solution is admixed with 40 ml of ethanol and 20 ml of propylene glycol to make a 5% composition.

EXAMPLE 8

O-acetylmandelic acid 2% cream is prepared as follows.

O-acetylmandelic acid 2 gm is dissolved in 5 ml of ethanol, and the solution is admixed with 93 gm of hydrophilic ointment, U.S.P. Continue agitation until a uniform consistency is obtained.

EXAMPLE 9

O-acetylmandelic acid 5% solution is prepared as follows.

O-acetylmandelic acid 5 gm is dissolved in 95 ml of a solution prepared from 3 parts of water, 5 parts of ethanol and 2 parts of propylene glycol by volume.

EXAMPLE 10

Use of a alpha or beta hydroxyacids or ketoacids as additives to enhance topical corticosteroid action is shown in the following example.

PART A

Sorbitan sesquioleate: 10 gm
Petrolatum: 15 gm
Mineral oil: 15 gm
Beeswax: 15 gm
Isopropyl myristate: 10 gm

PART B

Water: 23 ml
Propylene glycol: 5 ml

Sorbitol: 3 gm
Glycerol: 3 ml
Magnesium hydroxide: 0.1 gm

Heat both Part A and Part B to 80° C. Add Part B slowly to Part A with agitation.

After the mixture is congealed add 10% phosphoric acid 0.5 ml, aluminum chlorohydroxide 0.5 gm, hydrocortisone 1 gm and O-acetylmandelic acid 0.2 gm. This composition with a pH of 5.4 containing 1% hydrocortisone and 0.2% O-acetylmandelic acid.

EXAMPLE 11

Anhydrous composition containing two active ingredients is formulated as follows.

Glyceryl monostearate: 20 gm
Petrolatum: 15 gm
Mineral oil: 10 gm
Beeswax: 5 gm
Isopropyl myristate: 50 gm The above mixture is heated to 75° C. until it is completely melted. Hydrocortisone 1 gm and O-acetylmandelic acid 1 gm are added to the melt with agitation. Continue agitation until the mixture is congealed. This composition with a pH of 3.4 containing 1% of hydrocortisone and 1% of hydroxyacid.

EXAMPLE 12

Another example of an anhydrous composition containing two active ingredients is shown in the following.

Glyceryl monostearate: 20 gm
Petrolatum: 10 gm
Mineral oil: 10 gm
Isopropyl myristate: 60 gm The above mixture is heated to 75° C. until it is completely melted. Hydrocortisone-17-valerate 0.2 gm and O-acetylmandelic acid 0.1 gm are added to the melt with agitation. Continue agitation until the mixture is congealed. This composition with a pH of 4.7 containing 0.2% hydrocortisone-17-valerate and 0.1% hydroxyacid.

EXAMPLE 13

Use of alphahydroxyacids as additives to stabilize the unstable drug dithranol in topical compositions is illustrated in the following example.

Glyceryl monostearate: 20 gm
Petrolatum: 10 gm
Mineral oil: 10 gm
Isopropyl myristate: 60 gm The above mixture is heated to 75° C. until it is completely melted. Quinic acid 0.2 gm and dithranol 0.05 gm are added to the melt with agitation. Agitation is continued until the mixture is congealed to a yellowish cream. This composition with a pH of 6.4 contains 0.05% of dithranol stabilized with 0.2% of alpha hydroxyacid.

EXAMPLE 14

A therapeutic composition containing 10% alpha or beta hydroxyacids or ketoacids in a shampoo formulation is prepared as follows.

Quinic acid 10 gm is dissolved in 40 ml of water and 20 ml of propylene glycol. Concentrated ammonium hydroxide 4 ml and triethanolamine lauryl sulfate 26 ml are added to the mixture with agitation. Continue agitation until a uniform consistency is obtained.

EXAMPLE 15

O-Acetylmandelic peroxide may be synthesized as follows:

Ammonium carbonate 50 gm is dissolved in 100 ml of 30% hydrogen peroxide and the mixture is cooled externally with a salt-ice bath. O-Acetylmandelic acid chloride 125 ml is added slowly to the mixture with stirring. The temperature of the mixture is kept at 5°–10° C. throughout the whole period of reaction. The reaction mixture is stirred for an additional two hours at 5°–10° C. after the addition of O-acetylmandelic acid chloride. Water 600 ml is added to the reaction mixture, and the product which separates into the bottom layer is isolated as an oily syrup, 120 gm. The product is purified by dissolving in 200 ml of chloroform, washing with 200 ml of water, drying over anhydrous sodium sulfate and evaporating at 30° C. in a vacuum to remove chloroform. O-acetylmandelic peroxide thus synthesized is practically pure as shown by infrared spectroscopy and by thin-layer chromatography with a mobility of 0.47 on a solvent system of benzene: methanol, 1:1.

EXAMPLE 16

O-acetylmandelic peroxide 5% solution may be prepared as follows.

O-acetylmandelic peroxide 5 gm synthesized according to Example 15 is dissolved in 50 ml of ethanol, and the solution is mixed with 20 ml of propylene glycol and 25 ml of water.

EXAMPLE 17

O-acetylmandelic peroxide 5% gel may be prepared as follows.

O-acetylmandelic peroxide 5 gm is dissolved in 50 ml of ethanol, and the solution is mixed with 20 ml of propylene glycol and 25 ml of water. Hydroxypropylcellulose 1.5 gm is added to the mixture with agitation. Continue agitation until a uniform gel is formed.

TEST RESULTS

Dry skin (A) Severe Dry Skin

The involved skin in severe dry skin is hyperplastic (thickened) and has thick adherent scales. The degree of thickening is such that lesions are palpably and visually elevated. The thickened adherent scales cause the surface of involved skin to be markedly rough and uneven. These two attributes of thickness and texture can be quantified to allow objective measurement of degree of improvement from topically applied therapeutic test materials as follows:

| | Degree of Improvement | | | | |
|---|---|---|---|---|---|
| | None (0) | Mid (1+) | Moderate (2+) | Substantial (3+) | Complete (4+) |
| THICK-NESS | Highly elevated | Detectable reduction | Readily apparent reduction | Barely elevated | Normal thickness |
| TEX-TURE | Visibly rough | Palpably rough | Uneven but not rough | Slightly uneven | Visibly and palpably smooth |

By means of such parameters degrees of change in lesions can be numerically noted and comparisons made of one treated site to another.

In order to evaluate the hydroxyacids and their analogues of this invention a total of five patients with severe dry skin conditions or ichthyosis were treated with the compositions as described in the Examples.

Treated areas were of a size convenient for topical applications, i.e., circles 4 cm in diameter demarcated with a plastic ring of that size inked on a stamp pad. The medicinal cream, gel or ointments were topically applied by the patient in an amount (usually about 0.1 cubic milliliter) sufficient to cover the treatment site. Applications were made three times daily and without occlusive dressings. Application periods did not exceed three weeks, and applications were discontinued at any time when resolutions of the lesion on the treatment area was clinically judged to be complete. Clinical evaluations of degrees of improvement were made at daily intervals.

The test results on patients with severe dry skin are summarized on the following table.

| Topical effectiveness of hydroxyacids on severe dry skin | | |
|---|---|---|
| Compounds | Number of Patients | Therapeutic Effectiveness |
| 1. 2-hydroxy-4-(methylthio)-butanoic acid | 5 | 4+ |
| 2. 2-hydroxy-4-(methylsulfonyl)-butanoic acid | 4 | 3+ |
| 3. Quinic acid | 5 | 4+ |

(B) Common Dry Skin

Human subjects with mild to moderate degrees of dry skin conditions, as evidenced by dry, cracking or flaking of the skin were instructed to apply topically the lotion, cream or ointment of the present invention formulated according to the same Examples as in (A) on the affected skin areas. Twice daily topical application was continued for a few weeks. In all the ten human subjects tested, the feeling of the skin dryness disappeared after three to four days of topical treatment. In ten human subjects tested the rough and cracked skin usually became less pronounced within a week's time. Generally, the skin appeared normal and felt smooth after about two weeks of topical treatment.

The common dry skin conditions once restored to normal appearing skin remained improved for some time until causes of dry skin, such as low humidity, cold weather, detergents, soaps, chemicals, etc., again caused recurrence of the dry skin condition. On continued use it was also found that twice daily topical application of a composition of the present invention prevented the development of new dry skin lesions.

Psoriasis

The involved skin in psoriasis is hyperplastic (thickened), erythematous (red or inflamed), and has thick adherent scales. The degree of thickening is such that lesions are elevated up to 1 mm above the surface of adjacent normal skin; erythema is usually an intense red; the thickened adherent scales cause the surface of involved skin to be markedly rough and uneven. These three attributes of thickness, color and texture can be quantified to allow objective measurement of degree of improvement from topically applied therapeutic test materials as follows:

| | Degree of Improvement | | | | |
|---|---|---|---|---|---|
| | None (0) | Mid (1+) | Moderate (2+) | Substantial (3+) | Complete (4+) |
| Thickness | Highly elevated | Detectable reduction | Readily apparent reduction | Barely elevated | Normal thickness |
| Texture | Visibly rough | Palpably rough | Uneven but not rough | Slightly uneven | Visibly and palpably smooth |
| Color | Intense red | Red | Dark pink | Light pink | Normal skin color |

By means of such parameters degrees of change in psoriatic lesions can be numerically noted and comparisons made of one treated site to another.

Therapeutic compositions containing quinic acid or 2-hydroxy-4-(methyl sulfonyl) butanoic acid were prepared according to the Examples. Three patients having psoriasis participated in this study.

| Topical effectiveness of hydroxyacids on psoriasis | | |
|---|---|---|
| Compounds | Number of Patients | Therapeutic Effectiveness |
| 1. Quinic acid | 3 | 2+ |
| 2. 2-hydroxy-4-(methylsulfonyl)-butanoic acid | 3 | 3+ |

Acne

Twenty patients having comedones or moderate to severe papularpustular acne participated in this study. Therapeutic compositions containing O-acetylmandelic acid, O-acetylmandelic peroxide or 2-hydroxy-4-(methylsulfonyl) butanoic acid were prepared according to the Examples. The patients were instructed to apply topically the therapeutic compositions twice daily on affected areas of the skin for up to eight weeks. Standarized color photos were taken of the full face and/or each side of the face prior to initiating the treatment of the study and after 4 weeks and 8 weeks of topical treatment with the therapeutic compositions. The test results were determined both by clinical impression and also by comparison of the photos before and after treatment.

Eighteen of twenty patients showed substantial reduction in the number of acne lesions after eight weeks of topical treatment with O-acetylmandelic acid or O-acetylmandelic peroxide. Nine of twelve patients showed moderate reduction in the number of acne lesions after eight weeks of topical treatment with 2-hydroxy-4-(methylsulfonyl) butanoic acid.

Dandruff

Nine patients with moderate to severe dandruff problems participated in this study. Therapeutic compositions containing quinic acid, O-acetylmandelic acid, O-acetylmandelic peroxide or 2-hydroxy-4-(methylsulfonyl) butanoic acid were prepared according to the Examples. Patients were instructed to rub into the scalp the shampoo preparations containing the active ingredients. After each shampoo the patients were advised to apply topically the after-shampoo solutions containing the same active ingredients onto the scalp. This two-step topical treatment substantially reduced or prevented all signs of dandruff, i.e., formation of scales on the scalp in all nine patients. Relief was observed within about one to two weeks. On continued use it was also discovered that twice weekly topical application of the above preparations would prevent the development of dandruff.

Darier's Disease

A patient with Darier's Disease was instructed to apply topically three times daily to the lesions the therapeutic compositions containing 2-hydroxy-4-(methylthio)-butanoic acid or 2-hydroxy-4-(methylsulfonyl)-butanoic acid prepared according to the Examples. A substantial improvement as evidenced by the reduction in thickness and visibly and palpably smooth lesions was achieved after six weeks of topical treatment.

Palmar and Plantar Hyperkeratosis

Three patients with palmar or plantar hyperkeratosis secondary to chronic friction, or inflammation eczema were instructed to apply topically three times daily to the lesions the therapeutic compositions containing quinic acid, 2-hydroxy-4-(methylthio) butanoic acid or 2-hydroxy-4-(methylsulfonyl) butanoic acid prepared according to the Examples. A substantial to complete improvement as evidenced by the reduction in thickness, visibly and palpably smooth skin was achieved after four to six weeks of topical treatment.

Pruritus

Six patients with pruritus ani or persistent itching secondary to chronic eczema or other inflammatory disorders were instructed to apply topically three times daily to the lesions the therapeutic compositions containing O-acetylmandelic acid or O-acetylmandelic peroxide. Complete relief from itching was achieved in all the patients within a few days of topical treatment.

The invention may be embodied in other specific forms without departing from the spirit of essential characteristics thereof. The present embodiment is, therefore, to be considered in all respects as illustrative and not restrictive, the scope of the invention being indicated by the appended claims and all changes which come within the meaning and range of equivalency of the claims are, therefore, intended to be embraced therein.

What is claimed:

1. A therapeutic composition effective against skin disease conditions characterized by inflammation or disturbed keratinization comprising: at least one compound selected from the group consisting of:
2-hydroxy-3-methylpentanoic acid, 2,3-dihydroxybutanoic acid, 2-hydroxy-3-mercaptopropanoic acid, 3,3-dithiobis (2-hydroxypropanoic acid), 2-hydroxy-4-(methylthio)butanoic acid, 2-hydroxy-4-(methylsulfoxide)butanoic acid, 2-hydroxy-4-(methylsulfonyl)butanoic acid, 2-hydroxy-5-guanidopentanoic acid, 2,6-dihydroxyhexanoic acid, 2-hydroxy-6-aminohexanoic acid, 2,5,6-trihydroxyhexanoic acid, 2,5-dihydroxy-6-aminohexanoic acid, 2-hydroxy-3-(4-imidazolyl)propanoic acid, 2-hydroxy-3-(4-hydroxyphenyl)propanoic acid, 2-hydroxy-3-(3′ indolyl) propanoic acid, 2-hydroxy-4-mercaptobutanoic acid, 4,4′-dithiobis (2-hydroxybutanoic acid), 2,4-dihydroxybutanoic acid, 2-hydroxy-3-sulfinopropanoic acid, 3-aminolactic acid, 2,4-dihydroxybutanoic acid, 2-hydroxy-2-methyl-butanoic acid, 2,5-dihydroxypentanoic acid, 2-hydroxy-5-ureidopentanoic acid, 2-hydroxy-6-ureidohexanoic acid, 2-hydroxy-3-(5′-hydroxyindolyl)propanoic acid, 3-(3′,4′-dihydroxyphenyl)lactic acid, 3-(3′-iodo-4′-hydroxyphenyl) lactic acid, 3-(3′5′-diiodo-4′-hydroxyphenyl) lactic acid, hydroxy analogue of thyroxine having the formula:

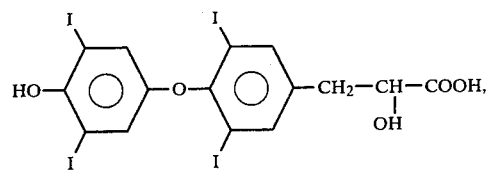

hydroxy analogue of thyronine having the formula:

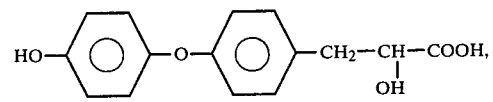

quinic acid, 3-hydroxypropanoic acid, glyceruric acid, threuric acid, erythreuric acid, xyluric acid, lyxuric acid, arabinuric acid, riburic acid, iduric acid, guluric acid, mannuric acid, altruric acid, alluric acid, taluric acid, 2-hydroxy-3-sulfonopropanoic acid, 2-hydroxy-3-thio-s-(3′-hydroxy-1′,1′,-dimethylpropyl) propanoic acid, P-hydroxyphenylglycolic acid, O-acetylmandelic, acid trihydroxy butanoic acid, tetrahydroxy pentanoic acid, pentahydroxyhexanoic acid and hexahydroxyheptanoic acid, or a salt thereof present in an effective amount in a pharmaceutically or cosmetically acceptable lotion, gel, shampoo, spray, stick, powder, cream or ointment.

2. The composition of claim 1 wherein said compound is present as a salt of an organic base or an inorganic base selected from the group consisting of sodium hydroxide, potassium hydroxide or ammonium hydroxide.

3. A threapeutic composition effective against skin disease conditions characterized by inflammation or disturbed keratinization comprising: at least one compound selected from the group consisting of:
2-hydroxysuccinamic acid, 2-hydroxyglutaric acid, 2-hydroxyglutaramic acid, 2-hydroxy-4-aminoglutaric acid, 2,4-dihydroxyglutaric acid, 2,3-dihydroxy-4-aminoglutaric acid, 2-hydroxy-3-thio-s-(1′-carboxy-2′-methylpropyl)propanoic acid, 2-hydroxyadipic acid, 2,6-dihydroxypimelic acid, 4-hydroxy-4-methylglutamic acid, 3,4-dihydroxyglutamic acid, 4-hydroxyglutamic acid, ribaric acid, arabaric acid, xylaric acid, lyxaric acid, allaric acid, altraric acid, mannaric acid, gularic acid, idaric acid and talaric acid or a salt thereof present in an effective amount in a pharmaceutically or cosmetically acceptable lotion, gel, shampoo, spray, stick, powder, cream or ointment.

4. The composition of claim 3 wherein said compound is present as a salt of an organic base or an inorganic base selected from the group consisting of sodium hydroxide, potassium hydroxide or ammonium hydroxide.

5. A therapeutic composition effective against skin disease conditions characterized by inflammation and disturbed keratinization comprising: at least one compound selected from the group consisting of:
acetopyruvic acid, acetyl pyruvic acid and β-fluoropyruvic acid or a salt thereof present in an effective amount in a pharmaceutically or cosmetically acceptable lotion, gel, shampoo, spray, stick, powder, cream, or ointment.

6. The composition of claim 5 wherein said compound is present as a salt of an organic base or an inorganic base selected from the group consisting of sodium hydroxide, potassium hydroxide or ammonium hydroxide.

7. A method for alleviating the symptoms of skin disease conditions characterized by inflammation or disturbed keratinization comprising:
topically administering to the afflicted individual a therapeutic composition containing an effective amount of at least one compound selected from the group consisting of:
2-hydroxy-3-methylpentanoic acid, 2,3-dihydroxybutanoic acid, 3,3-dithiobis (2-hydroxypropanoic acid), 2-hydroxy-4-(methylthio) butanoic acid, 2-hydroxy-4-(methylsulfoxide)butanoic acid, 2-hydroxy-4-(methylsulfonyl)butanoic acid, 2-hydroxy-5-quanidopentanoic acid, 2,6-dihydroxyhexanoic acid, 2-hydroxy-6-aminohexanoic acid, 2,5,6-trihydroxyhexanoic acid, 2,5-dihydroxy-6-aminohexanoic acid, 2-hydroxy-3-(4-imidazolyl)-propanoic acid, 2-hydroxy-3-(4-hydroxyphenyl)-propanoic acid, 2-hydroxy-3-(3'-indolyl)propanoic acid, 2-hydroxy-4-mercaptobutanoic acid, 4,4'-dithiobis(2-hydroxybutanoic acid), 2,4-dihydroxybutanoic acid, 2-hydroxy-3-sulfinopropanoic acid, 3-aminolactic acid, 2,4-dihydroxybutanoic acid, 2-hydroxy-2-methyl-butanoic acid, 2,5-dihydroxypentanoic acid, 2-hydroxy-5-ureidopentanoic acid, 2-hydroxy-6-ureidohexanoic acid, 2-hydroxy-3-(5'-hydroxyindolyl) propanoic acid, 3-(3'-4'-dihydroxyphenyl)lactic acid, 3-(3'-iodo-4'-hydroxyphenyl)lactic acid, 3-(3'5'-diiodo-4'-hydroxyphenyl)lactic acid, hydroxy analogue of thyroxine having the formula

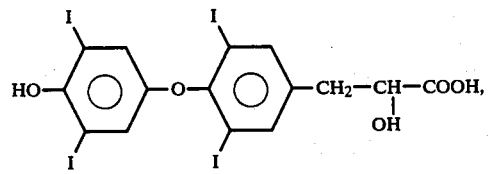

hydroxy analogue of thyronine having the formula:

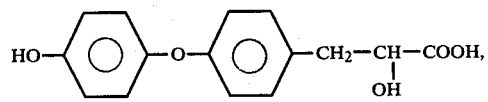

quinic acid, 3-hydroxypropanoic acid, glyceruric acid, threuric acid, erytheuric acid, xyluric acid, lyxuric acid, arabinuric acid, riburic acid, iduric acid, guluric acid, mannuric acid, altruric acid, alluric acid, taluric acid, 2-hydroxy-3-sulfonopropanoic acid, 2-hydroxy-3-thio-s-(3'hydroxy-1',1',-dimethylpropyl) propanoic acid, P-hydroxyphenylglycolic acid O-acetylmandelic trihydroxy butanoic acid, tetrahydroxy pentanoic acid, pentahydroxyhexanoic acid, and hexahydroxyheptanoic acid in a pharmaceutically or cosmetically acceptable vehicle.

8. The method of claim 7 wherein said compound is present as a salt of an organic base or an inorganic base selected from the group consisting of sodium hydroxide, potassium hydroxide or ammonium hydroxide.

9. A method for alleviating the symptoms of skin disease conditions characterized by inflammation or disturbed keratinization comprising:
topically applying to the afflicted individual a therapeutic composition containing an effective amount of at least one compound selected from the group consisting of:
2-hydroxysuccinamic acid, 2-hydroxyglutaric acid, 2-hydroxyglutaramic acid, 2-hydroxy-4-aminoglutaric acid, 2,4-dihydroxyglutaramic acid, 2-hydroxy-4-aminoglutaric acid, 2-hydroxy-3-thio-s-(1'carboxy-2'-methylpropyl)propanoic acid, 2-hydroxyadipic acid, 2,6-dihydroxypimelic acid, 4-hydroxy-4-methylgutamic acid, 3,4-dihydroxyglutamic acid, 4-hydroxyglutamic acid, ribaric acid, arabaric acid, xylaric acid, lyxaric acid, allaric acid, altraric acid, mannaric acid, gularic acid, idaric acid and talaric acid or a salt thereof in a pharmaceutically or cosmetically acceptable vehicle.

10. The method of claim 9 wherein said compound is present as a salt of an organic base or an inorganic base selected from the group consisting of sodium hydroxide, potassium hydroxide or ammonium hydroxide.

11. A method for alleviating the symptoms of skin disease conditions characterized by inflammation or disturbed keratinization comprising:
topically administering to the afflicted individual a therapeutic composition containing an effective amount of at least one compound selected from the group consisting of:
acetopyruvic acid, acetyl pyruvic acid and β-fluoropyruvic acid or a salt thereof in a pharmaceutically or cosmetically acceptable vehicle.

12. The method of claim 11 wherein said compound is present as a salt of an organic base or an inorganic base selected from the group consisting of sodium hydroxide, potassium hydroxide or ammonium hydroxide.

* * * * *

UNITED STATES PATENT AND TRADEMARK OFFICE
CERTIFICATE OF CORRECTION

PATENT NO. : 4,363,815

DATED : December 14, 1982

INVENTOR(S) : Yu et al

It is certified that error appears in the above—identified patent and that said Letters Patent is hereby corrected as shown below:

Col 6, line 30, "expressed" should read --expected--;
Col. 6, line 54, --6.-- should appear before "2,3-dihydroxy...".

Signed and Sealed this

Second Day of August 1983

[SEAL]

Attest:

GERALD J. MOSSINGHOFF

Attesting Officer   Commissioner of Patents and Trademarks

UNITED STATES PATENT AND TRADEMARK OFFICE
CERTIFICATE OF CORRECTION

PATENT NO. : 4,363,815

DATED : December 14, 1982

INVENTOR(S) : Ruey J. Yu and Eugene J. Van Scott

It is certified that error appears in the above-identified patent and that said Letters Patent is hereby corrected as shown below:

Col. 16, line 31 (claim 1), "O-acetylmandelic, acid" should read --O-acetylmandelic acid,--.

Col. 18, line 15 (claim 7) "O-acetylmandelic" should read --, O-acetylmandelic acid,--.

*Signed and Sealed this*

*Seventeenth* Day of *January 1984*

[SEAL]

Attest:

GERALD J. MOSSINGHOFF

*Attesting Officer*   *Commissioner of Patents and Trademarks*